(12) United States Patent  
Worley

(10) Patent No.: US 8,224,463 B2
(45) Date of Patent: *Jul. 17, 2012

(54) CORONARY SINUS LEAD FOR PACING THE LEFT ATRIUM

(75) Inventor: Seth Worley, Lancaster, PA (US)

(73) Assignee: Oscor Inc., Palm Harbor, FL (US)

( * ) Notice: Subject to any disclaimer, the term of this patent is extended or adjusted under 35 U.S.C. 154(b) by 17 days.

This patent is subject to a terminal disclaimer.

(21) Appl. No.: 12/398,822

(22) Filed: Mar. 5, 2009

(65) Prior Publication Data

US 2010/0114286 A1 May 6, 2010

Related U.S. Application Data

(63) Continuation of application No. 11/358,644, filed on Feb. 21, 2006, now abandoned, which is a continuation-in-part of application No. 11/144,447, filed on Jun. 3, 2005, now abandoned.

(51) Int. Cl.
*A61N 1/05* (2006.01)
(52) U.S. Cl. .............................. 607/125; 607/9; 607/126
(58) Field of Classification Search ............... 607/9, 125
See application file for complete search history.

(56) References Cited

U.S. PATENT DOCUMENTS

| 4,154,247 | A | * | 5/1979 | O'Neill | 607/125 |
| 5,879,295 | A | * | 3/1999 | Li et al. | 600/373 |
| 6,096,036 | A | * | 8/2000 | Bowe et al. | 606/41 |

* cited by examiner

*Primary Examiner* — Niketa Patel
*Assistant Examiner* — Alyssa M Alter
(74) *Attorney, Agent, or Firm* — Scott D. Wofsy; Edwards Wildman Palmer LLP

(57) ABSTRACT

A pacing lead for implantation in a coronary sinus having an opening and a wall defining an interior and presenting a diameter dimension. The pacing lead includes an elongated lead body, a resilient fixation element, and at least one electrode on either the lead body or the fixation element. The fixation element extends from the pacing portion and defines a loop structure laterally adjacent the pacing portion. The loop structure presents a predetermined width dimension greater than the diameter dimension of the coronary sinus, wherein when the loop structure is inserted into the opening of the coronary sinus, the loop structure is laterally compressed by the wall of the coronary sinus and the electrode is biased against the wall of the coronary sinus.

20 Claims, 16 Drawing Sheets

CORONARY SINUS LEAD FOR PACING THE LEFT ATRIUM

RELATED APPLICATIONS

This application is a continuation of U.S. patent application Ser. No. 11/358,644, entitled CORONARY SINUS LEAD FOR PACING THE LEFT ATRIUM, filed Feb. 21, 2006, which is a continuation-in-part of U.S. patent application Ser. No. 11/144,447, entitled CORONARY SINUS LEAD FOR PACING THE LEFT ATRIUM, filed Jun. 3, 2005, both of said applications hereby fully incorporated herein by reference.

FIELD OF THE INVENTION

The present invention relates generally to pacing leads. More particularly, the present invention relates to pacing leads for stable pacing of the left atrium through the coronary sinus.

BACKGROUND OF THE INVENTION

Pacing to the left atrium is important for successful bi-atrial pacing. The pacing to the left atrium is usually accomplished by placing a pacing lead into the coronary sinus, which is a venous structure accessible through the right atrium of the heart and serves to drain the coronary veins. The coronary sinus is a curved, generally tubular structure typically having a lesser radius of curvature (the inner side of the curved tube) and a greater radius of curvature (the outer side of the curved tube). The coronary sinus is generally wider at its ostium and tapers inwardly away from the ostium towards the distal portions of the coronary sinus. The ostium of the coronary sinus is located at the juncture of the right atrium and the right ventricle.

To pace the left atrium, a pacing lead can be positioned so that an electrode contacts the wall of the coronary sinus closest to the left atrium. Because the coronary sinus is in electrical contact with the left atrium, by pacing the coronary sinus at this position, one can also pace the left atrium. The pacing lead generally is advanced to the ostium of the coronary sinus through the right atrium portion of the right heart. For effective pacing, electrodes on the pacing lead should be in constant electrical conductive contact with the wall of the coronary sinus, preferably the left atrial side of the coronary sinus. Conductivity is preferably sufficient so as to enable a pacing voltage of 3 volts or less.

To accomplish constant wall contact, different pacing lead configurations have been used to assist in the placement and retention of the pacing lead in the desired position. These prior leads, however, all have certain drawbacks making them not entirely satisfactory. For example, leads have been used in which a body of the lead is pre-formed to have a sinusoidal or helical configuration enabling the lead to expand into contact with the walls of the coronary sinus and retain the lead. Examples of such pre-formed coronary sinus leads are disclosed in U.S. Pat. No. 5,423,865 to Bowald et al. and U,S. Pat. No. 5,476,498 to Ayers. Such shapes, however, if not carefully sized to the diameter of the coronary sinus do not necessarily bias the electrodes against the wall of the coronary sinus with sufficient force to ensure good electrical connectivity resulting in instability and high pacing thresholds. Moreover, with helical shape leads, the electrodes may be difficult to properly position relative to the coronary sinus wall for optimal contact and thresholds.

Referring to FIGS. 1a-1f, specific examples of pre-formed coronary sinus leads are depicted and described in U.S. Pat. No. 6,321,123 to Morris et al, which is incorporated herein by reference. Pacing leads 20 according to Morris et al. generally include a proximal lead portion 21 with a first curved portion 22, a second curved portion 24, a tip electrode 26, and additional electrodes 28 longitudinally disposed relative to proximal lead portion 21. A sheath and straightening stylet or guidewire is used to insert the lead 20 tip first into a coronary sinus. Once the sheath and lead 20 are within the coronary sinus, the sheath is removed and the lead 20 resiliently flexes toward its pre-formed shape. The pre-formed "J" in the lead 20 can cause the tip 26 to be pressed up against the wall of the coronary sinus as depicted in FIGS. 1c and 1d, but only if the width of the pre-formed pacing lead 20 is greater than that of the coronary sinus. The tip and other electrodes, however, may not be in an optimal geometric relationship with the wall of the coronary sinus, since the lead cannot fully assume its preformed shape. Moreover, the biasing force exerted by the lead has both a laterally directed component, annotated as $F_1$ in the figures, and a longitudinally directed component, annotated as $F_2$ in the figures. The longitudinally directed component of the biasing force tends to urge the lead longitudinally backward in the coronary sinus toward the ostium, thereby reducing lead stability.

When the coronary sinus is wider than the pacing lead 20, the lead may assume a loop shape longitudinally disposed relative to proximal lead portion 21 as depicted in FIGS. 1b, 1e and 1f. In this case, the longitudinally directed component of the biasing force $F_2$ is generally relatively less due to the contact of the lead with the coronary sinus wall laterally opposite the tip 26, but the resilience of the lead may provide little or no laterally directed biasing force $F_1$ for good electrical conductivity, and in some cases the tip electrode can lose contact with the wall of the coronary sinus altogether. This can lead to higher voltage requirements, greater instability and higher pacing and sensing thresholds.

Referring to FIG. 2, there are also other pacing leads 30 that can be used to pace the left atrium through the coronary sinus, such as the Medtronic Attain® Bipolar OTW Lead Model No. 4194 and leads as disclosed in U.S. Pat. No. 5,683,445 to Swoyer, both of which are incorporated herein by reference. The pacing lead 30 generally includes a first curved portion 32, a second curved portion 34, and a tip electrode 36. As depicted in FIG. 2, the angle 31 at the first curve 32 is greater than ninety degrees. Again, a sheath and stylet are used to insert the lead 30 tip first into a coronary sinus. Once the sheath and lead 30 are within the coronary sinus, the sheath and stylet are removed and the lead 30 takes its pre-formed shape, enabling the tip electrode 36 to contact the walls of the coronary sinus if the diameter of the coronary sinus is less than the width of the pre-formed shape of the lead. Again however, using these leads to pace the coronary sinus presents the same problems inherent with the leads according to Morris et al. as described above.

The present inventor has recognized that prior art leads and fixation methods provide a success rate of 60% or less when used to pace the left atrium via the coronary sinus. Hence, there is still a need for a lead and fixation method assuring stable pacing of the left atrium through the coronary sinus. Because the general problems discussed above have not been addressed by conventional pacing leads, there is a current need for pacing leads addressing the problems and deficiencies inherent with conventional designs.

SUMMARY OF THE INVENTION

The pacing lead of the various embodiments of the present invention substantially addresses the aforementioned problems of conventional designs by providing lead shapes and methods of pacing lead deployment that assure that the electrodes of the lead are firmly in electrical conductive contact with the wall of the coronary sinus so as to enable pacing voltages of 3 volts or less. In an embodiment, the improved pacing is accomplished because as the lead is advanced into the coronary sinus, a resilient fixation element preformed in a prolapsed position so as to be laterally adjacent the lead body, is laterally compressed by the walls of the coronary sinus as it is advanced into the coronary sinus. The resilience of the fixation element biases the lead body and portions of the fixation element against the wall of the coronary sinus, thereby improving electrical conductivity between the coronary sinus wall and electrodes disposed on the lead body or on the biased portions of the fixation element. In addition, in embodiments with a tip electrode, the prolapsed fixation element insures that the tip electrode is fixed relative to the coronary sinus closest to the left atrium, thus resulting in lower pacing voltages and thresholds and higher pacing stability.

In another embodiment, the lead has a pacing portion and a resilient fixation element extending distally from the pacing portion. The pacing portion includes a proximal electrode and a distal electrode. The fixation element is preformed so as to be doubled-back or prolapsed along the pacing portion, forming a loop structure. The width dimension of the preformed loop structure is predetermined so as to be larger than the diameter of the coronary sinus. When the loop structure is advanced into the coronary sinus, the loop is compressed in the width direction so that the electrodes of the pacing portion are biased against the wall of the coronary sinus by the resilience of the fixation element, thereby improving electrode conductive contact with the wall of the coronary sinus and resulting in improved stability and lower pacing and sensing thresholds. The electrodes of the pacing portion are biased against the wall of the coronary sinus (lesser curvature) where the left atrium is in proximity to the coronary sinus because the pacing lead proximal to the fixation element conforms naturally to the lesser curvature of the coronary sinus.

According to an embodiment, a pacing lead for implantation in a coronary sinus having an opening and a wall defining an interior and presenting a diameter dimension, includes an elongated lead body having a pacing portion with at least one electrode and a resilient fixation element. The fixation element extends from the pacing portion and defines a loop structure laterally adjacent the pacing portion. The loop structure presents a predetermined width dimension greater than the diameter dimension of the coronary sinus, wherein when the loop structure is advanced into the opening of the coronary sinus, the loop structure is laterally compressed by the wall of the coronary sinus and the at least one electrode is biased against the wall of the coronary sinus.

According to an embodiment of a method according to the invention, a pacing lead is provided having a lead body with a resilient fixation element extending from a distal end thereof. The resilient fixation element is preformed in a prolapsed configuration so as to form a loop laterally adjacent the lead body. According to the method, the prolapsed form of the fixation element is deployed with the lead positioned outside of the ostium of the coronary sinus. The fixation element is then advanced into the coronary sinus so that the loop structure of the fixation element is laterally compressed by the wall of the coronary sinus, thereby biasing electrodes on the lead body or fixation element against the wall of the coronary sinus.

A feature and advantage of an embodiment of the invention is that the left atrium can be paced by directing the tip electrode towards the left atrium side of the coronary sinus.

A feature and advantage of an embodiment of the invention is that assuring constant contact between the lead electrodes and the walls of the coronary sinus can increase the stability of the fixation and pacing.

A feature and advantage of an embodiment of the invention is that the design of the pacing lead enables use on various sized coronary sinuses without sacrificing stability or pacing/sensing thresholds.

A feature and advantage of an embodiment of the invention is a method of pacing lead deployment assuring constant contact between the lead electrodes and the walls of the coronary sinus.

A feature and advantage of an embodiment of the invention is that the left atrium can be paced by biasing one or more lead electrode against the wall of the coronary sinus using a resilient fixation element of the lead.

A feature and advantage of an embodiment of the invention is that the resilient fixation element of the lead may or may not contain electrodes for sensing and pacing the left atrium via the coronary sinus.

DETAILED DESCRIPTION OF THE DRAWINGS

Figure 1A:
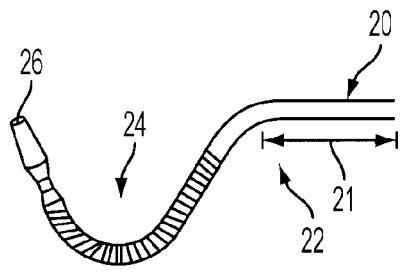
FIG. 1a is a fragmentary elevational view of a prior art coronary sinus pacing lead.
Figure 1B:
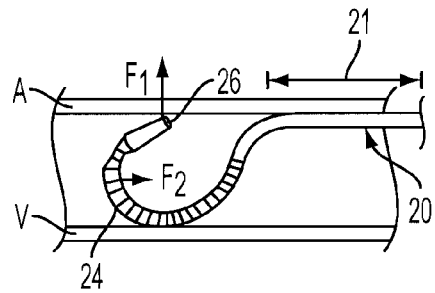
FIG. 1b-1f are fragmentary cross-sectional views of a coronary sinus depicting prior art coronary sinus pacing leads being inserted into the coronary sinus.
Figure 1C:
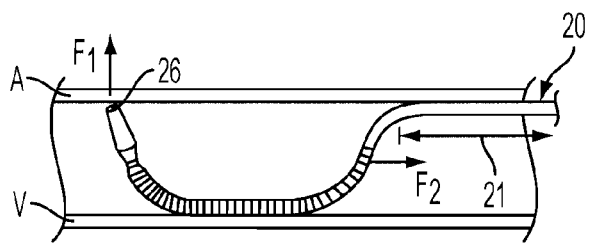
Figure 1D:
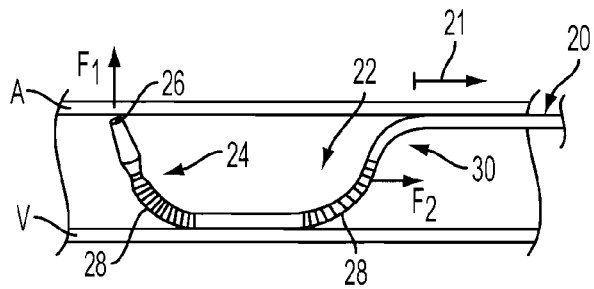
Figure 1E:
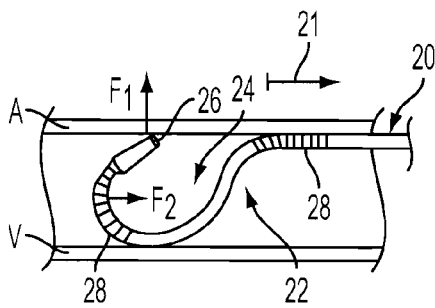
Figure 1F:
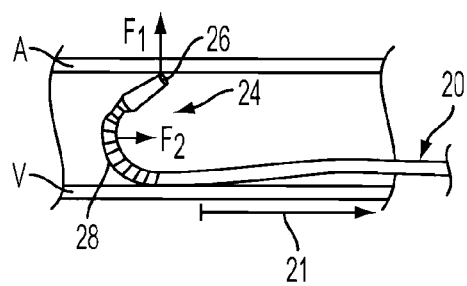
Figure 2:
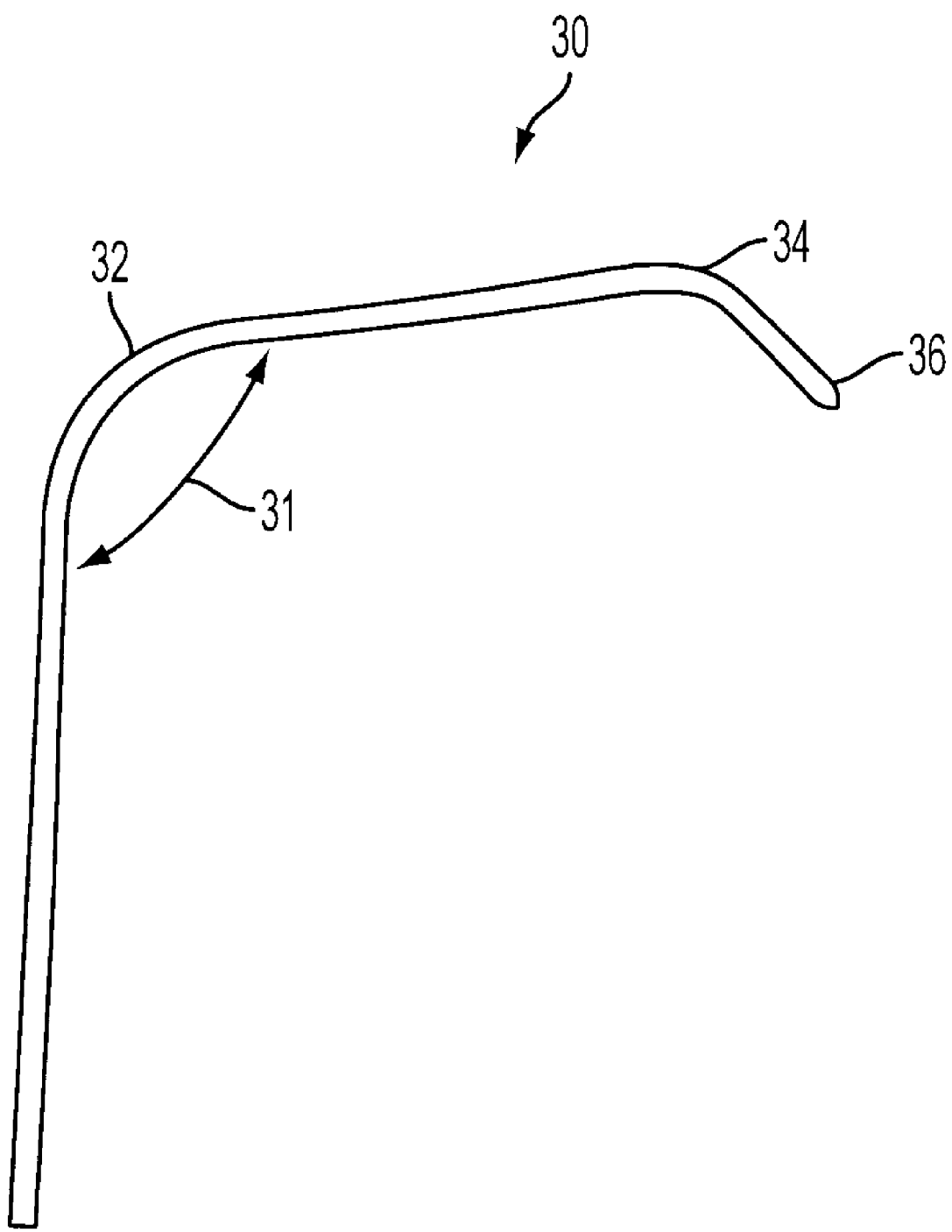
FIG. 2 is a fragmentary elevational view of a prior art left-ventricle pacing lead.
Figure 3:
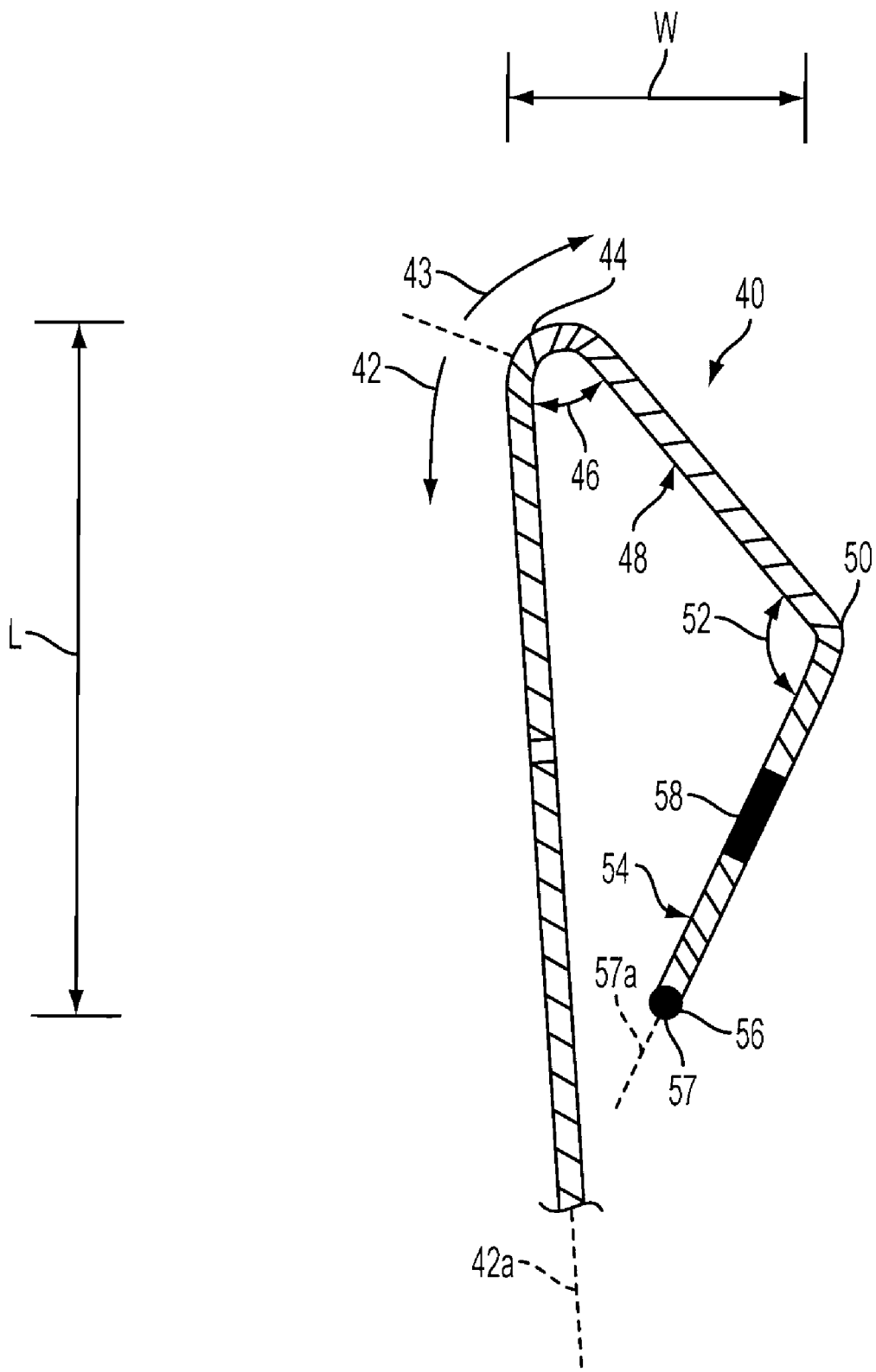
FIG. 3 is a fragmentary elevational view of a coronary sinus pacing lead according to an embodiment of the present invention.

Referring to FIG. 3, a pacing lead 40 according to the various embodiments of the present invention generally includes a proximal lead portion 42 presenting a lead axis 42a terminating in the fixation element 43 of the pacing lead at a first or proximal curve 44 having a first angle 46, a second or distal curve 50 having a second angle 52, and a tip 57 with a tip electrode 56 and presenting a longitudinal lead tip axis 57a. Lead 40 is preformed in a prolapsed configuration, with fixation element 43 doubled back so as to be laterally adjacent proximal lead portion 42 forming a loop structure 57a. A first section 48 is generally defined between the first and second curves 44, 50 and a second section 54 is generally defined between the second curve 50 and the tip electrode 56. The pacing lead 40 may also include additional curves and sections disposed between the first and second curves. The pacing lead 40 can also include additional curves and sections disposed between the tip of the pacing lead and the second curve. Fixation element 43 can also be configured in a continuous curve with a variety of radius arcs. Pacing leads are generally known in the art and are disclosed in U.S. Pat. No. 6,321,123 to Morris et al. and U.S. Pat No. 5,683,445 to Swoyer, both of which are incorporated herein by reference in their entirety.

The pacing lead 40 can also include one or more electrodes 58 disposed at any desired point on the proximal lead portion 42 or fixation element 43. The pacing lead 40 can further include a stylet 60 slidably disposed in the lead to initially straighten the preformed shape and which then may be withdrawn to the start of the fixation element to enable the preformed shape to develop and to selectively maintain the stiffness of the pacing lead 40 as the lead 40 is advanced into and positioned within the coronary sinus. It will also be appreciated that the shape of tip electrode 56 may be modified as desired, for example by maximizing contact surface area, to enable better contact with the wall of the coronary sinus and resultantly better performance.

The respective lengths of the first and second sections 48, 54 and the first and second angles 46, 52 between the first and second sections 48, 54 of the pacing lead 40 can be selected so that the tip electrode 56 will be in constant contact with the left atrial wall of the coronary sinus, i.e., to maximize contact between the tip electrode 46 and the left atrial wall of the coronary sinus. The overall length L and width W of the first and second sections 48, 54 can also be selected so that the tip electrode 56 will be in constant contact with the left atrial wall of the coronary sinus. The dimensions of the pacing lead according to exemplary embodiments of the present invention can be seen in Table I. Generally, the width of the pacing lead is preferably from about 10% to 200% greater than the diameter of the coronary sinus, more preferably from about 25% to about 75% greater than the diameter of the coronary sinus, and most preferably about 50% greater than the diameter of the coronary sinus for stability and good electrical contact.

TABLE I

Pacing lead dimensions according to various exemplary embodiments.

| | Range | First Exemplary Embodiment | Second Exemplary Embodiment |
|---|---|---|---|
| Lead Width (French) | 2 F to 9 F | 5 F ± 1 F | 5 F ± 1 F |
| Width - W (mm) | 2.0 to 20.0 | 7.0 ± 5.0 | 7.0 ± 5.0 |
| Length - L (mm) | 5.0 to 60.0 | 30.0 ± 5.0 | 30.0 ± 5.0 |
| First Section (mm) | 2.0 to 30.0 | 10 ± 5.0 | 20.0 ± [10.0 cm] |
| Second Section (mm) | 2.0 to 30.0 | 10 ± 5.0 | 20.0 ± [10.0 cm] |
| First angle* (degrees) | 90-165 | 45 ± 5 | 45 ± 5 |
| Second angle* (degrees) | 105-165 | 120 ± 30 | 120 ± 30 |

*Pre-formed angle prior to insertion into the coronary sinus.

While dimensions of the pacing lead 40 according to exemplary embodiments of the present invention are listed in Table I, one skilled in the art will recognize that changes may be made in form and detail of the dimensions without departing from the spirit and the scope of the invention. Therefore, the exemplary embodiments listed in Table I should be considered in all respects as illustrative and not restrictive.

Figure 4:
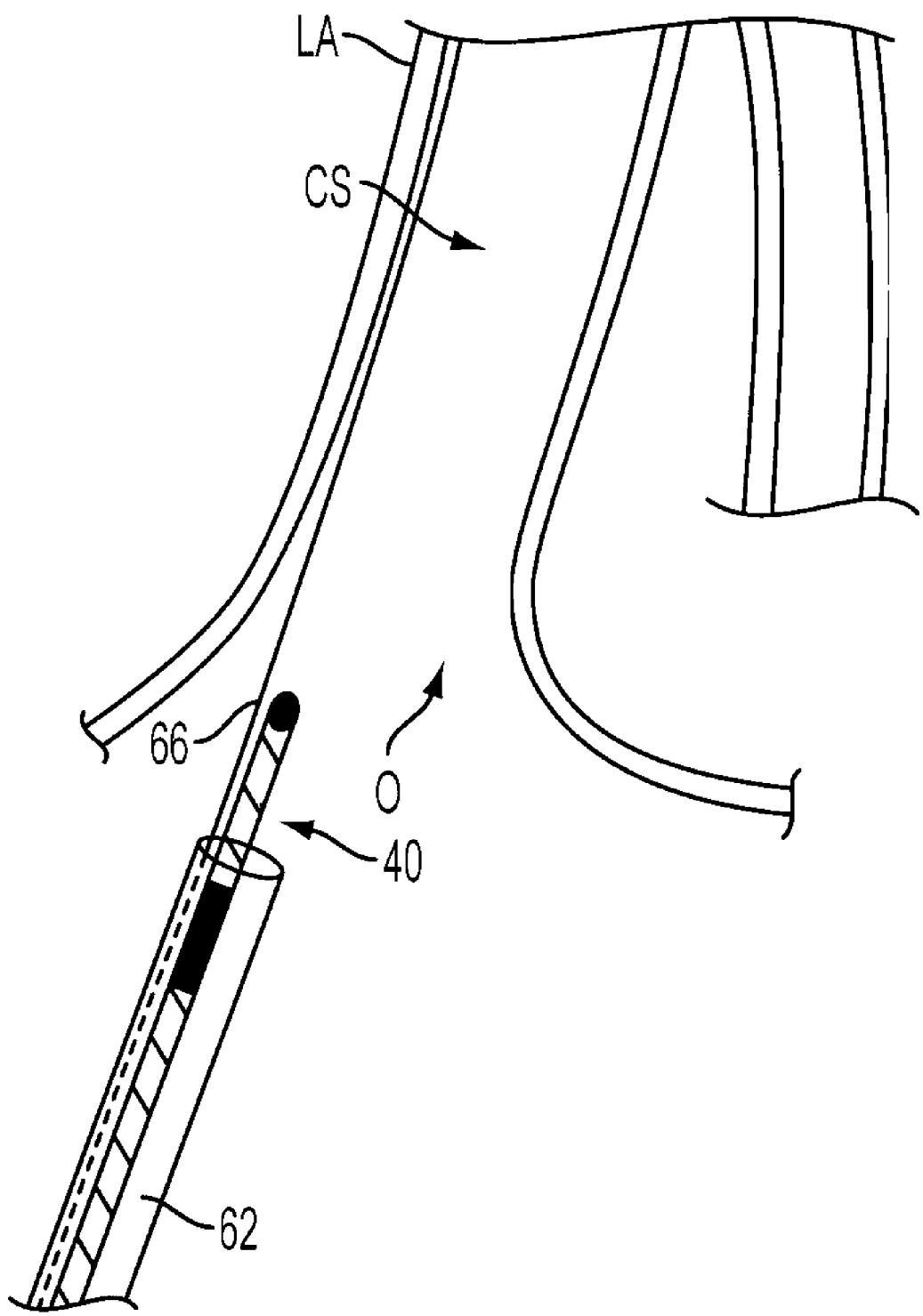
FIG. 4 is a fragmentary cross-sectional view of a coronary sinus depicting a coronary sinus pacing lead according to an embodiment of the present invention prior to being inserted into the coronary sinus.
Figure 5:
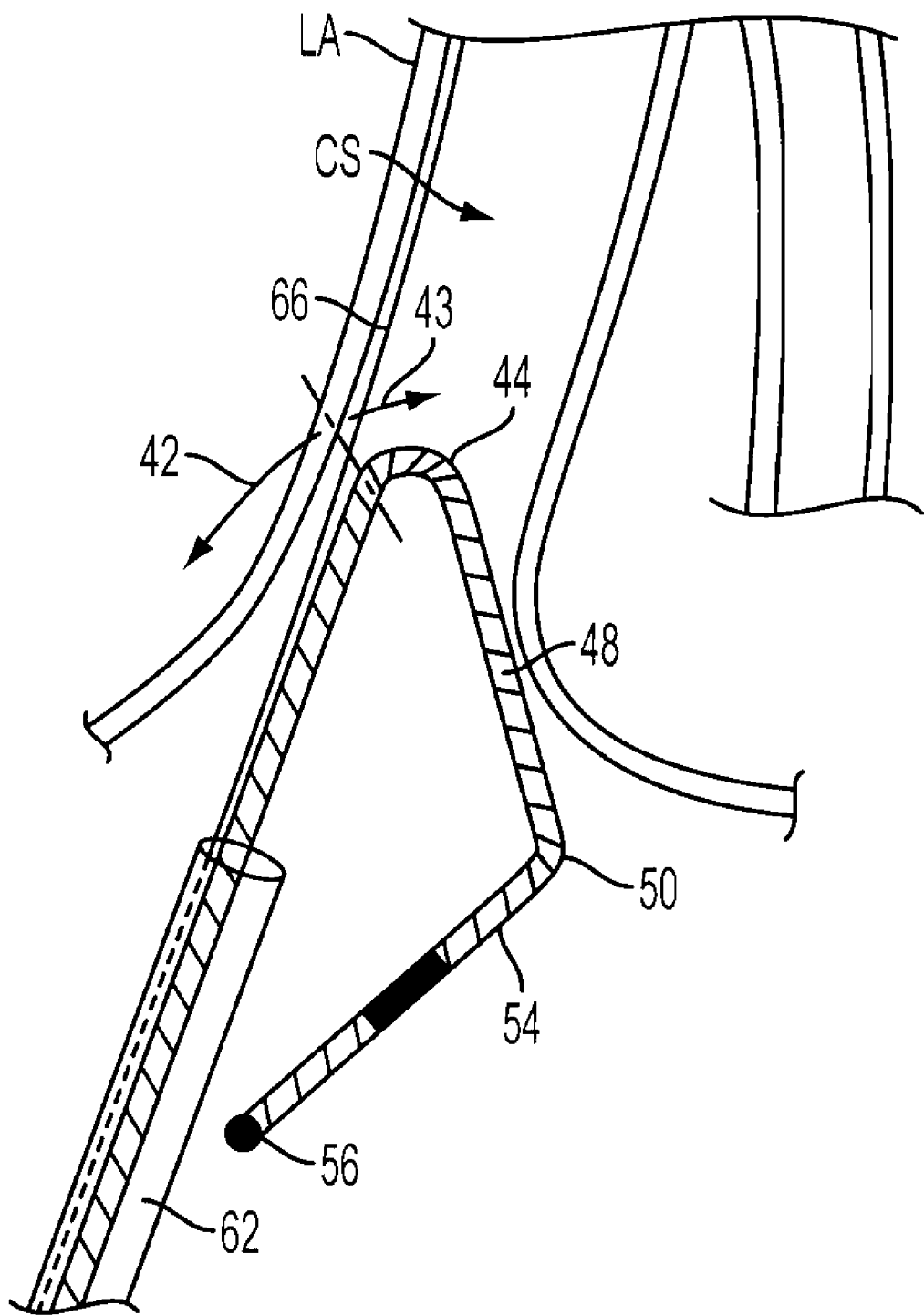
FIG. 5 is a fragmentary cross-sectional view of a coronary sinus depicting a coronary sinus pacing lead according to an embodiment of the present invention being inserted into the coronary sinus.
Figure 6:
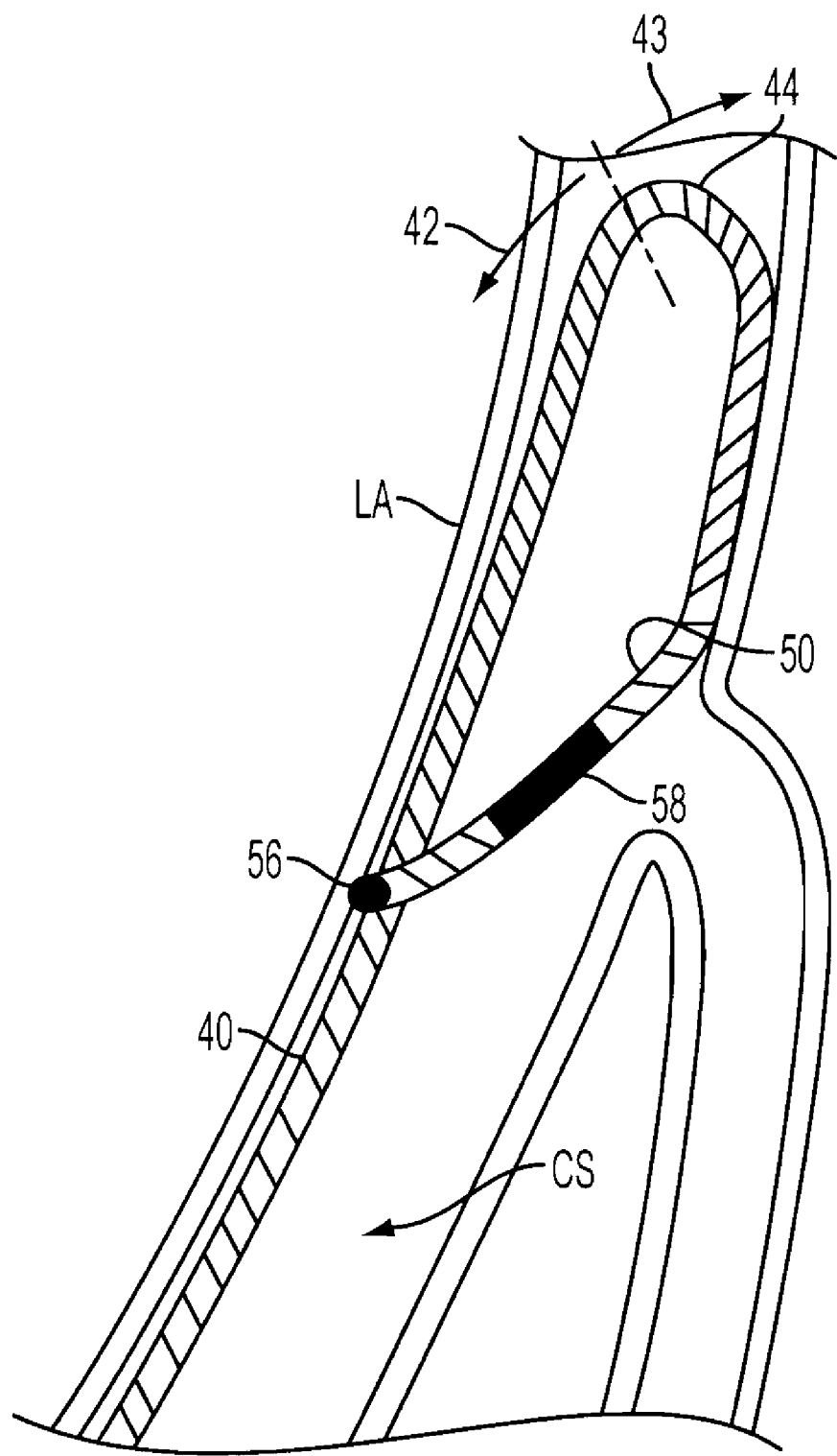
FIG. 6 is a fragmentary cross-sectional view of a coronary sinus depicting a coronary sinus pacing lead according to an embodiment of the present invention inserted into the coronary sinus.

Referring to FIGS. 4-6, implanting the pacing lead 40 into the coronary sinus can be accomplished by first inserting a stylet 60 into the pacing lead 40 and then advancing the pacing lead 40 with stylet 60 towards the ostium of the coronary sinus. Introducers for accessing the coronary sinus of the heart can be seen in U.S. Patent Application Publication Nos. 2003/0208141A1, 2004/0019359A1, and 2003/0208220A1, each to Worley et al., which are incorporated herein by reference. The implantation can be done using a guide wire supported guiding catheter 62 having a sheath 64 and guide support wire 66. A guide wire supported guiding catheter 62 is disclosed, for example, in U.S. Pat. No. 6,714,823, which is incorporated herein by reference. Alternatively, where the coronary sinus is of a smaller diameter, or where it is desired to pace the smaller diameter distal portion of the coronary sinus, pacing lead 40 may be inserted tip first using a sheath and stylet.

To implant the pacing lead 40 using a guiding catheter 62, one end of the guide wire 66 is first inserted deep into the coronary sinus. The other end of the guide wire 66 is operably coupled to the sheath 64 of the guiding catheter 62. The guide wire 66 can then maintain the positioning of the sheath 64 proximate the ostium of the coronary sinus.

Once the sheath 64 is held into place proximate the ostium of the coronary sinus, the stylet 60 of the pacing lead 40 is withdrawn out of the pacing lead 40 to a position proximate the first or proximal bend 44 of the pacing lead 40. The pacing lead 40 can then be advanced out of the sheath 64 to deploy the preformed loop of fixation element 43 while maintaining the stylet 60 at its position proximate the first bend 44 of the lead 40.

After the pacing lead 40 has been deployed out of the sheath 64 so that the lead 40 takes its pre-formed loop shape, the stylet 60 is kept at the first bend 44 of the pacing lead 40 while the lead 40 and stylet 60 are advanced into the coronary sinus, proximal bend 44 first. As stated above in Table I, in a first embodiment of the present invention, the first angle 46 between the first and second sections 48, 54, in its pre-formed configuration, is approximately 120 degrees.

As the pacing lead 40 is inserted into the ostium of the coronary sinus, the first angle 46 will compress or decrease until the tip electrode 56 comes into contact with the wall of the coronary sinus. Once this happens, the second angle 52 between the first and second sections 48, 54 will increase, e.g., to approximately one hundred and fifty degrees, due to compressive forces placed on the tip 56 as the pacing lead 40 progresses into the narrowing structure of the coronary sinus. In other words, in this wedged position, the walls of the coronary sinus flatten the distal curve 50 as the lead 40 is advanced into the tapering tubular structure of the coronary sinus. The tapering shape of the coronary sinus maximizes the contact between the tip electrode 56 and left atrium side of the coronary sinus.

Figure 7:
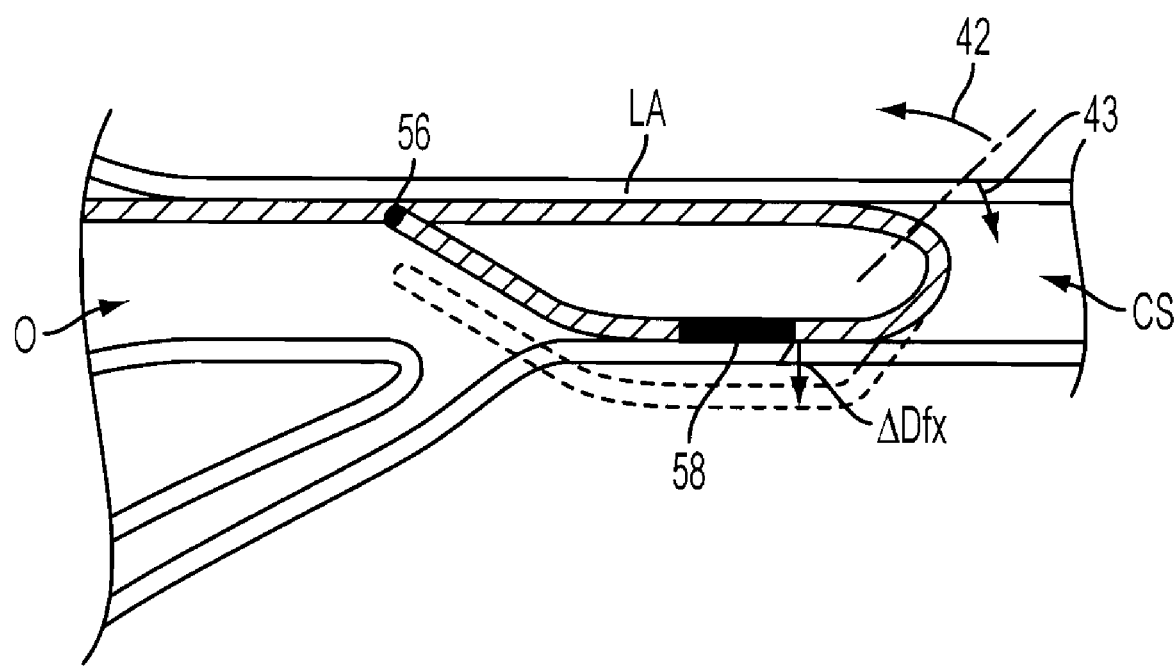
FIG. 7 is a fragmentary cross-sectional view of a coronary sinus depicting a coronary sinus pacing lead according to an embodiment of the present invention inserted into the coronary sinus.

By compressing the proximal and distal curves 44, 50, the lead 40 folds over and the tip electrode 56 is pressed against the left atrial side of the coronary sinus, thus improving the contact between the tip electrode 56 and the wall of the coronary sinus. Contact between the tip electrode 26 and the coronary sinus is maintained as the pacing lead 40 expands to assume its natural, expanded state. The contact results in lower pacing voltages and thresholds and higher pacing stability. The contact also inhibits any movement of the pacing lead 40 due to the heart beating and breathing of the patient once it is in its place within the coronary sinus. In this position, the coil or ring electrode 58 also has improved contact with the wall of the coronary sinus, as depicted in FIG. 7.

In an alternative embodiments depicted in FIGS. 8-14, lead 40 generally includes lead body 67 with pacing portion 68 and with fixation element 70 extending distally from lead body 67. Lead body 67 generally includes inner body 72 defining central lumen 74, inner conductor 76 which is electrically coupled with distal electrode 78, inner insulative sheath 80, outer conductor 82 which is electrically coupled with proximal electrode 84, and outer insulative sheath 86. Electrodes 78, 84, may be structured as rings 88 encircling lead 40, may be dorsal protuberances 90, or may be any other suitable structure enabling electrical coupling with the wall of the coronary sinus. Conductors 76, 82, may be coiled wire as commonly used in the art, or may be any other suitable generally flexible conductive structure. Inner body 72 and insulative sheathes 80, 86, may be formed from silicone, polyurethane, or other resilient biocompatible material.

Figure 9:
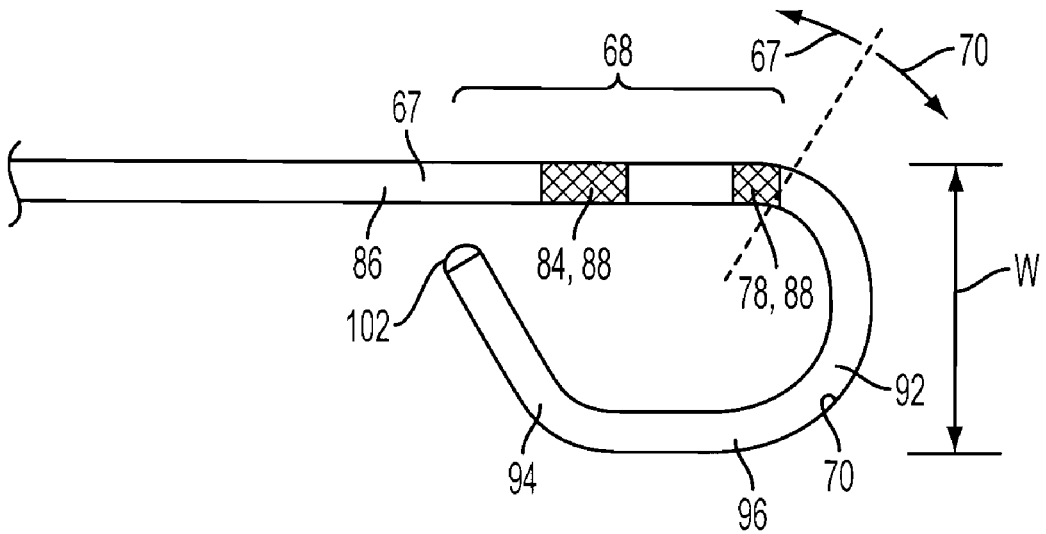
FIG. 9 is a fragmentary elevation view of a coronary sinus pacing lead according to an embodiment of the present invention.
Figure 10:
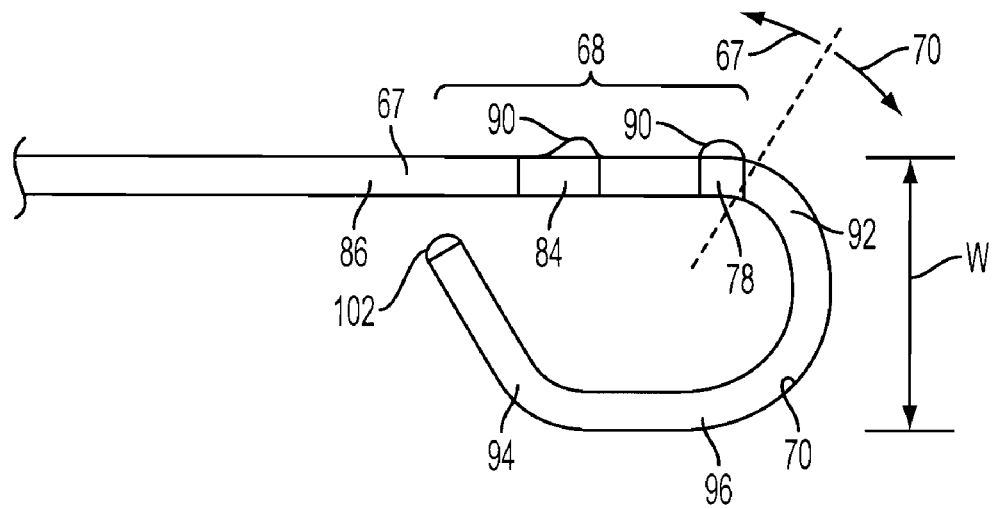
FIG. 10 is a fragmentary elevation view of a coronary sinus pacing lead according to an embodiment of the present invention.
Figure 11:
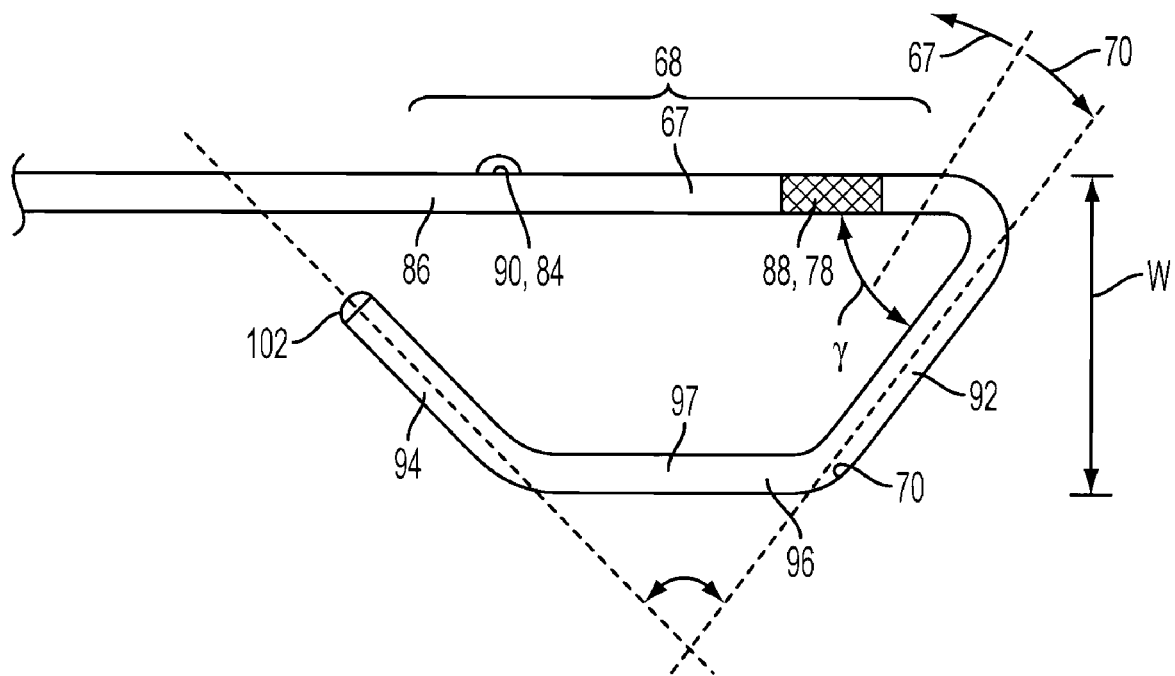
FIG. 11 is a fragmentary elevation view of a coronary sinus pacing lead according to an embodiment of the present invention.

As depicted in FIGS. 8-14, fixation element 70 may be integral with inner body 72 of lead body 67. According to the invention, fixation element 70 is preformed with a proximal portion 92 and distal portion 94, which together define a loop structure 96 laterally adjacent lead body 67. Loop structure 96 presents a width dimension, annotated "W" in the figures. As depicted, either or both of proximal portion 92 and distal portion 94 may be generally arcuate in shape or may be generally straight. In embodiments of the invention, a straight portion 97 may be interposed between proximal portion 92 and distal curved 94 as depicted in FIG. 11. Additionally, as depicted in FIG. 15, a short opposite bend 99 may be included between pacing portion 68 and proximal portion 92 to improve electrode contact with the coronary sinus wall when lead 40 is implanted.

Figure 12:
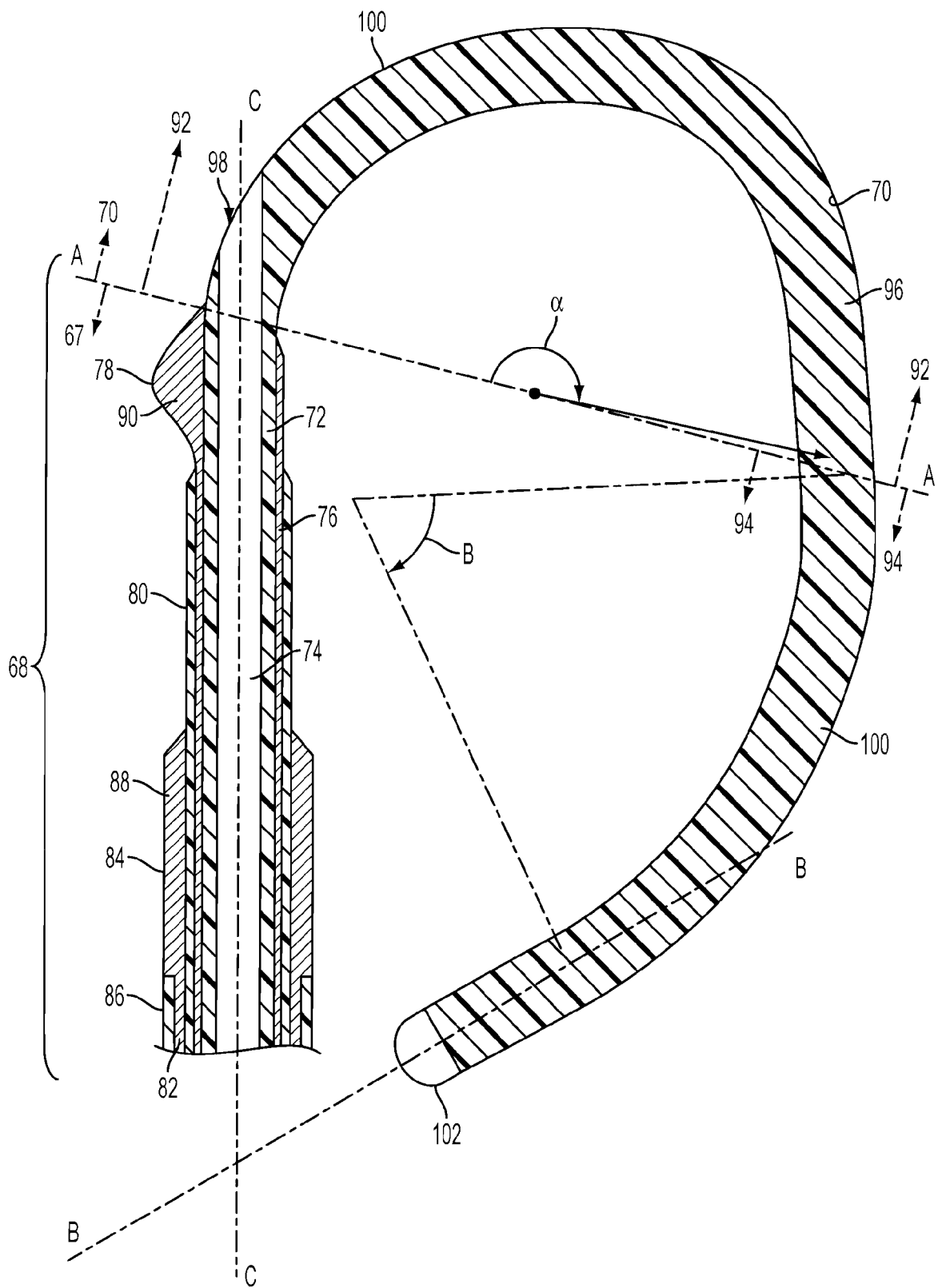
FIG. 12 is a fragmentary cross-sectional view of the coronary sinus lead of FIG. 8, taken along a longitudinal axis of the lead.

In embodiments where proximal and distal portions 92, 94, are arcuate as depicted for example in FIG. 12, proximal portion 92 desirably subtends an angle α of at least about 120 degrees and preferably about 180 degrees, and distal portion 94 subtends an angle of between about 40 and about 90 degrees. In embodiments where proximal and distal portions 92, 94, are generally straight as depicted for example in FIG. 11, proximal portion 92 preferably forms an angle γ with pacing portion 68 of less than 90 degrees. Distal portion 94 preferably forms an angle δ with respect to proximal portion 92 of between about 90 and about 150 degrees.

Figure 8:
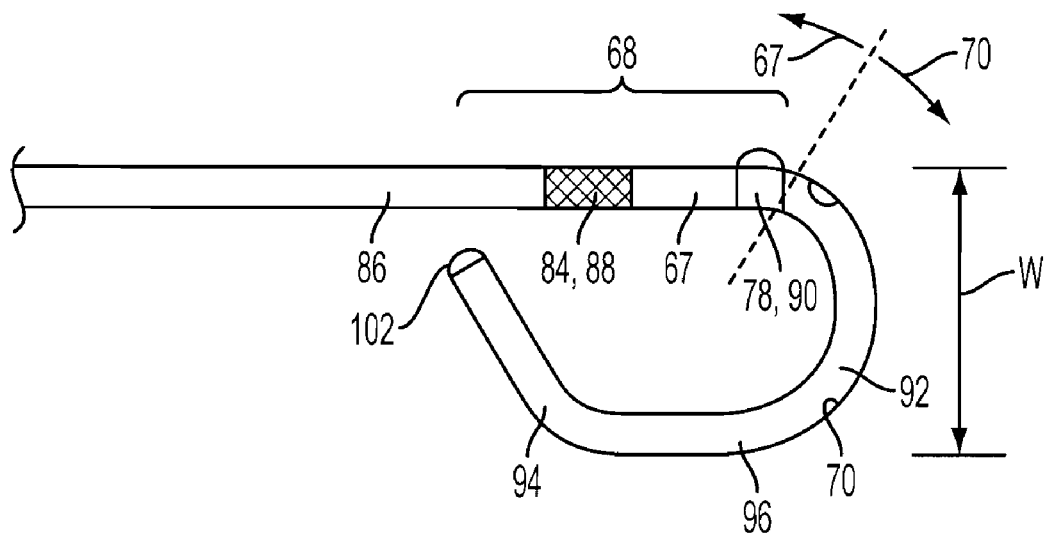
FIG. 8 is a fragmentary elevation view of a coronary sinus pacing lead according to an embodiment of the present invention.
Figure 13:
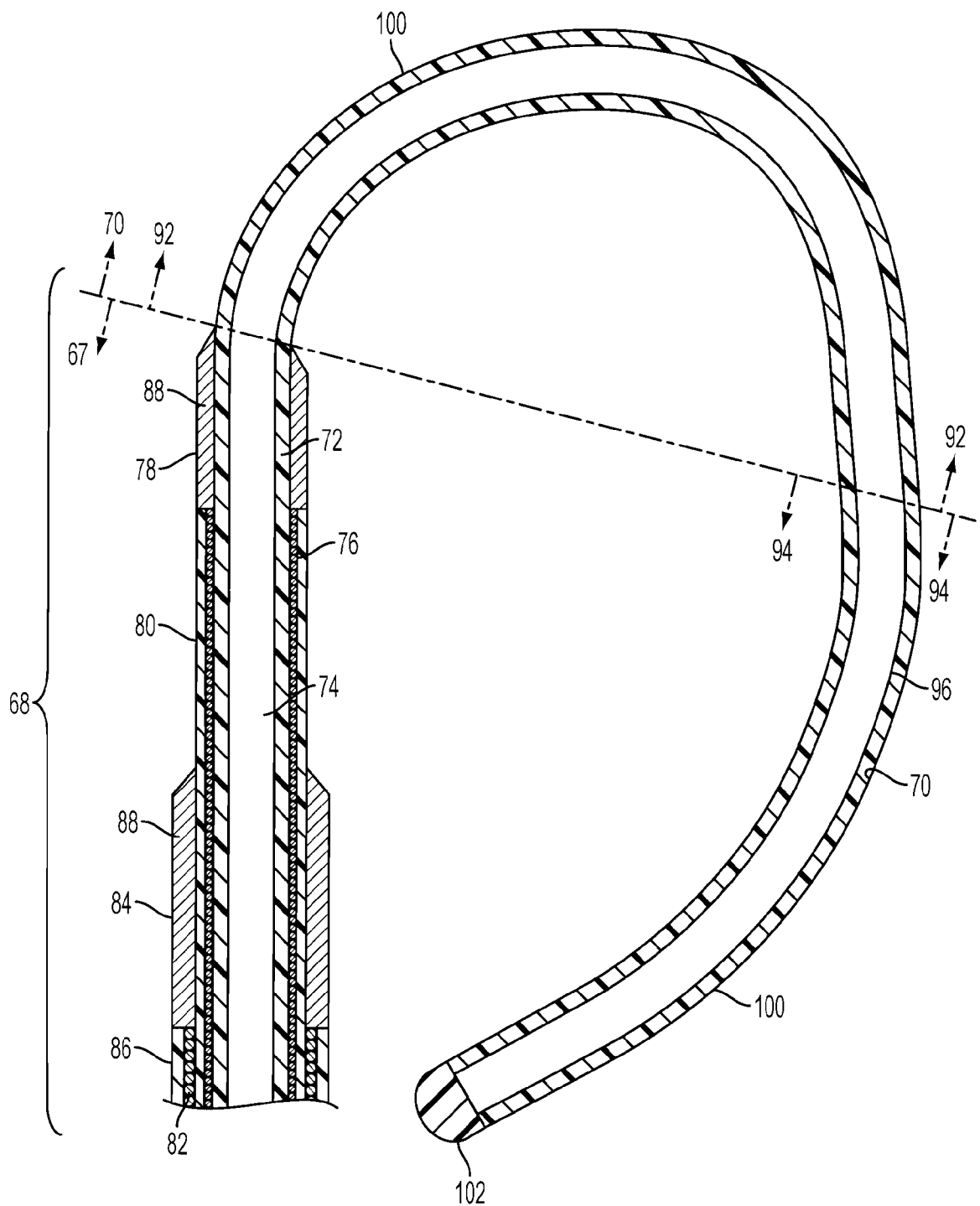
FIG. 13 is a fragmentary cross-sectional view of the coronary sinus lead of FIG. 9, taken along a longitudinal axis of the lead.
Figure 14:
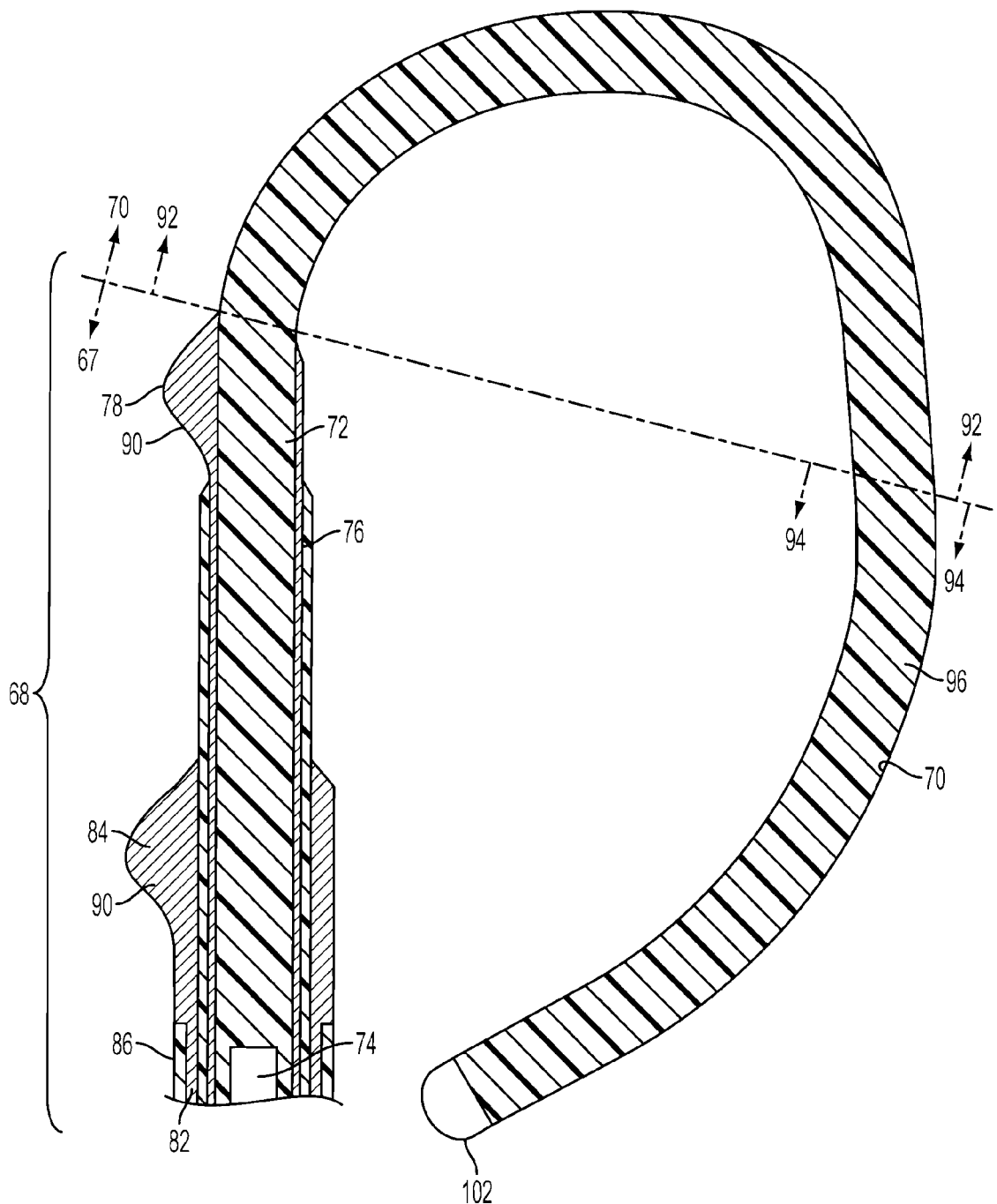
FIG. 14 is a fragmentary cross-sectional view of the coronary sinus lead of FIG. 10, taken along a longitudinal axis of the lead.
Figure 15:
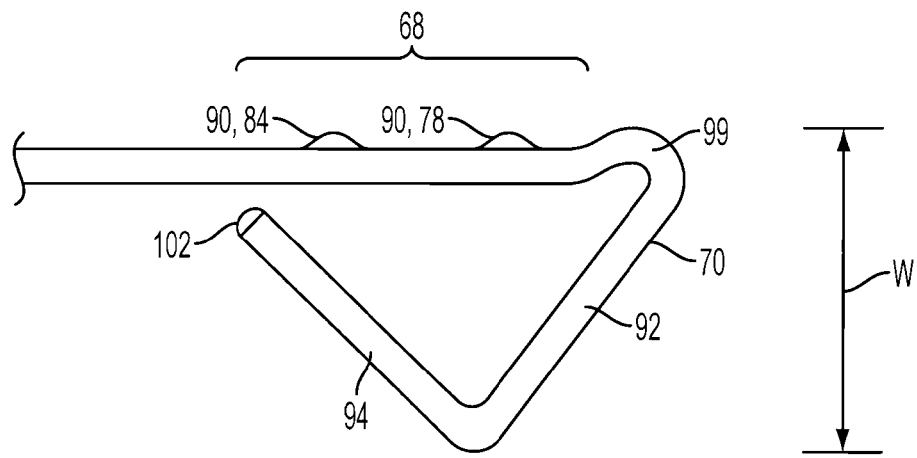
FIG. 15 is a fragmentary elevation view of the coronary sinus pacing lead according to an embodiment of the present invention.

Central lumen 74 may terminate in pacing portion 68 as depicted in FIGS. 10 and 14, may extend into fixation element 70, terminating in an aperture 98 leading to the outside surface 100 of the lead as depicted in FIGS. 8 and 12, or may extend through to tip 102 as depicted in FIGS. 9 and 13. It will be readily appreciated that in the embodiment of FIGS. 8 and 12, aperture 98 may be positioned and dimensions so that when fixation element 70 is straightened, aperture 98 is partially or fully closed. In some embodiments, lead 40 is packaged with fixation element 70 held straight with a straightening member (not depicted). The straightening member is removed prior to or during insertion of lead 40 to enable fixation element 70 to assume its preformed shape.

The lateral biasing force exerted by the resilience of the fixation element is a function of the material properties, the cross-sectional dimension of the fixation element, and the amount of lateral deflection, annotated in the figures as $\Delta D_{fx}$ of the fixation element. The amount of lateral deflection of the fixation element will vary depending on the diameter of the coronary sinus, and will generally be between about 0.5 centimeters and 12 centimeters, most typically from about 1.5 centimeters to about 6 centimeters. It will be appreciated that the magnitude of lateral biasing force may be predetermined by adjusting the material properties and dimensions of the fixation element using known principles of engineering. Generally, it is desirable if the fixation element provides between about 1 gram to about 30 grams of biasing force and more desirably between about 3 grams to about 10 grams when fixed in the coronary sinus.

Figure 16:
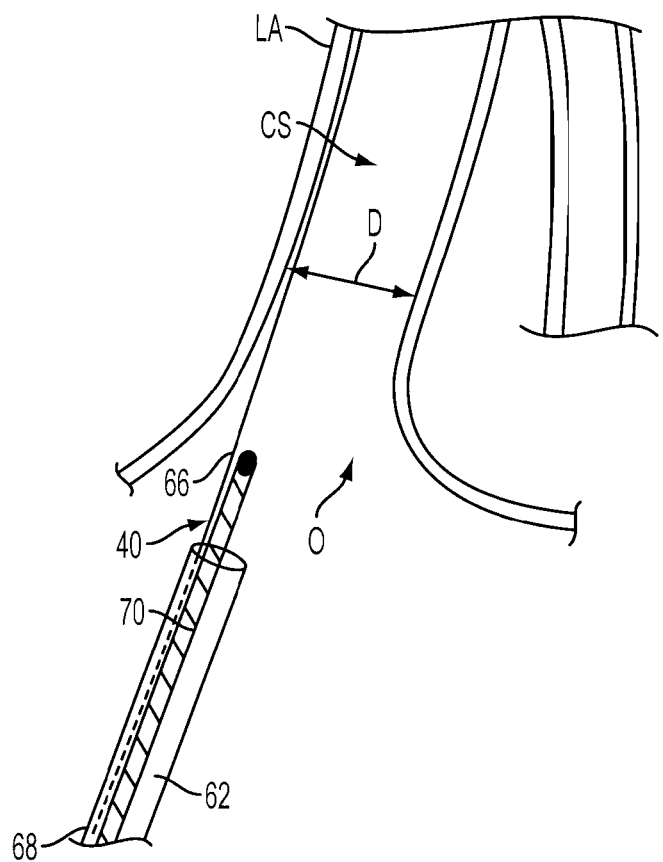
FIG. 16 is a fragmentary cross-sectional view of a coronary sinus depicting a coronary sinus pacing lead according to an embodiment of the present invention in a straightened orientation in a sheath prior to being inserted into the coronary sinus.
Figure 16A:
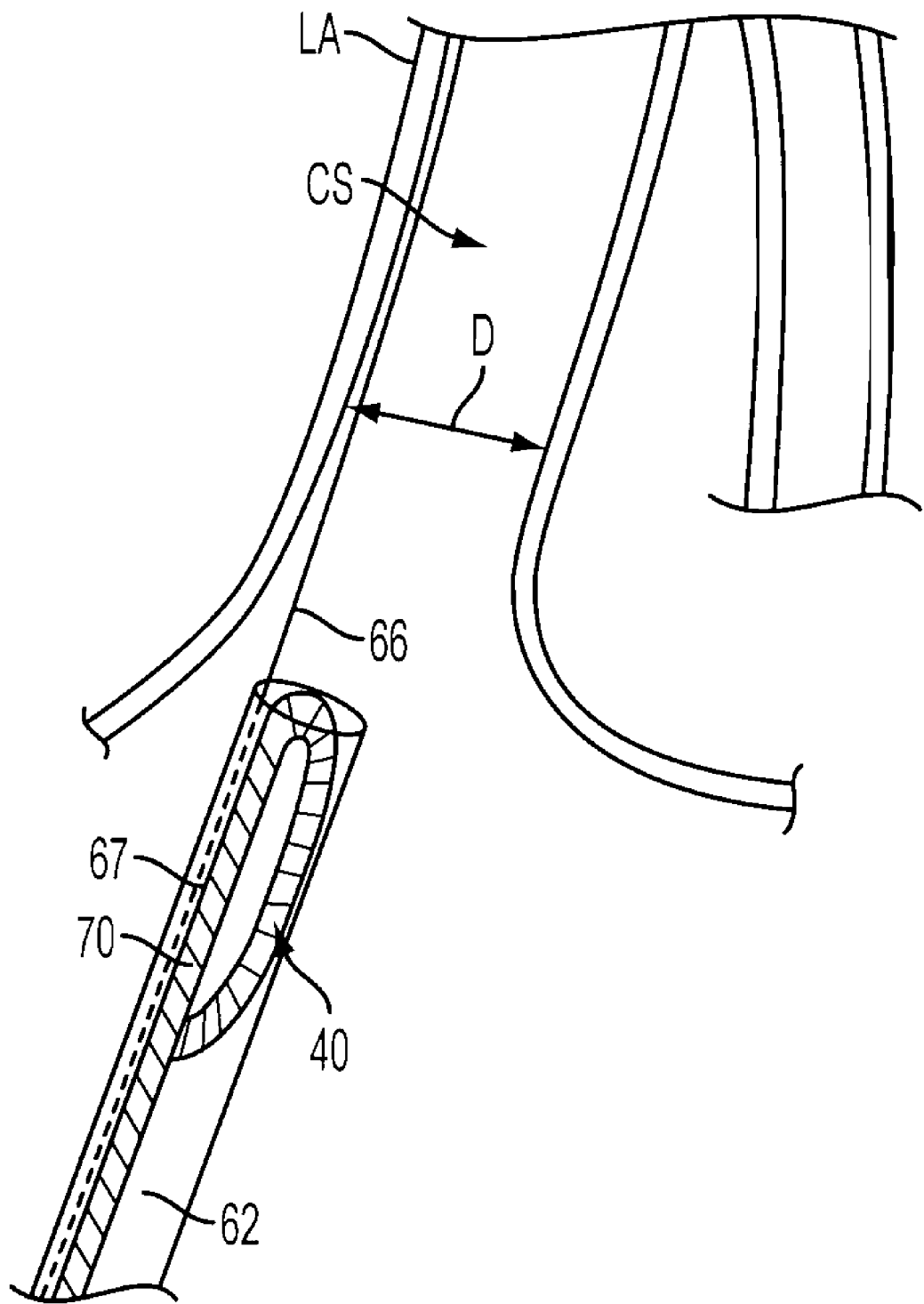
FIG. 16a is a fragmentary cross-sectional view of a coronary sinus depicting a coronary sinus pacing lead according to an embodiment of the present invention in an alternative prolapsed orientation in a sheath prior to being inserted into the coronary sinus.

Again, to implant the pacing lead 40 using a guiding catheter 62, one end of the guide wire 66 is first inserted deep into the coronary sinus as depicted in FIGS. 16 and 16a. The other end of the guide wire 66 is operably coupled to the sheath 64 of the guiding catheter 62. The guide wire 66 can then maintain the positioning of the sheath 64 proximate the ostium of the coronary sinus. Stylet 60 is inserted in central lumen 74 of lead 40 and the lead is advanced into sheath 64 in a straightened orientation as depicted in FIG. 16 or alternatively in a prolapsed orientation as depicted in FIG. 16a. Alternatively, in the embodiment of FIG. 12, lead 40 may be advanced into sheath 64 with guide wire 66 extending through aperture 98 and central lumen 74. In this embodiment, central lumen 74 also accommodates stylet 60 to enable lead 40 to be advanced along the guide wire.

Figure 17:
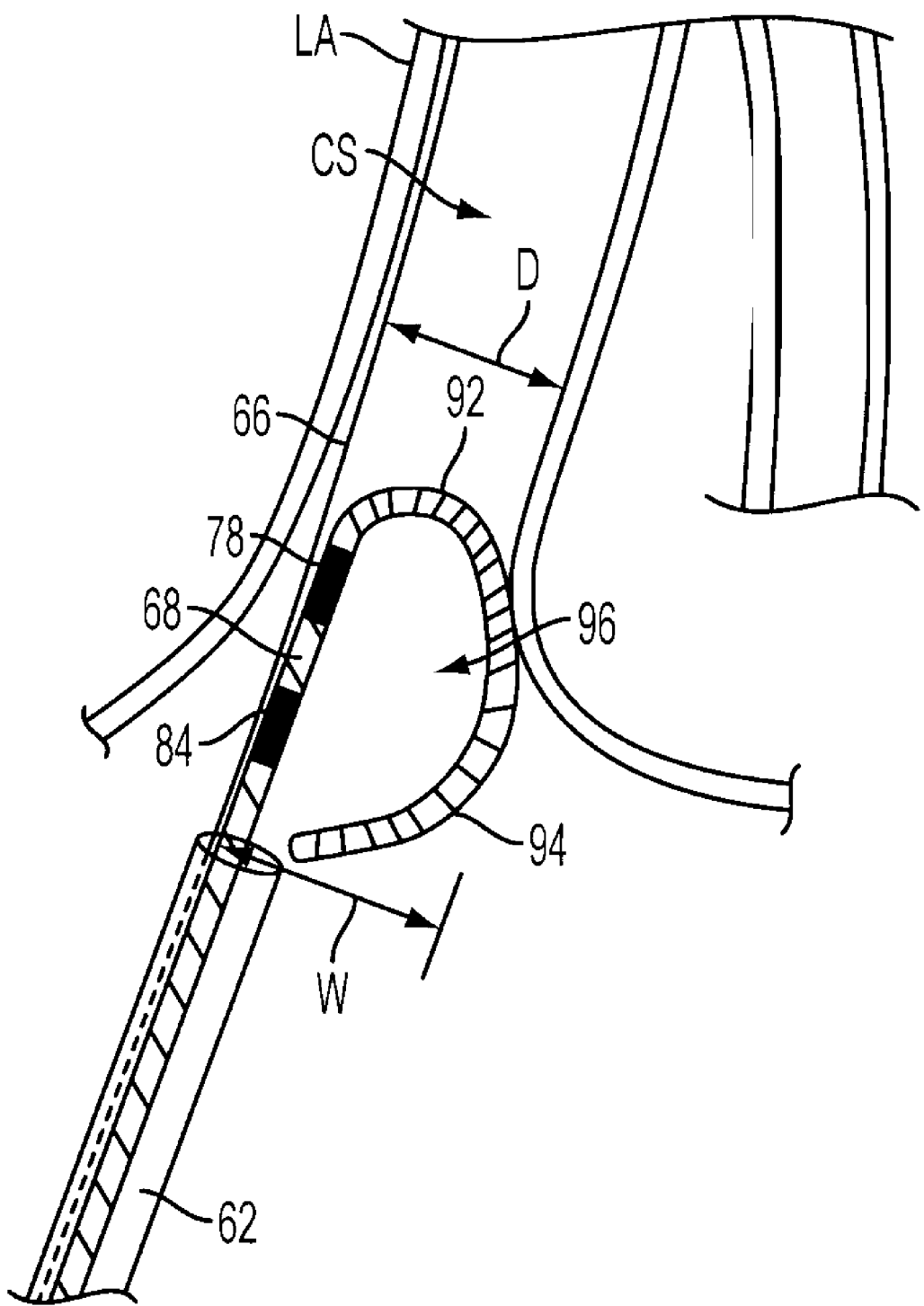
FIG. 17 is a fragmentary cross-sectional view of a coronary sinus depicting a coronary sinus pacing lead according to an embodiment of the present invention being inserted into the coronary sinus.
Figure 18:
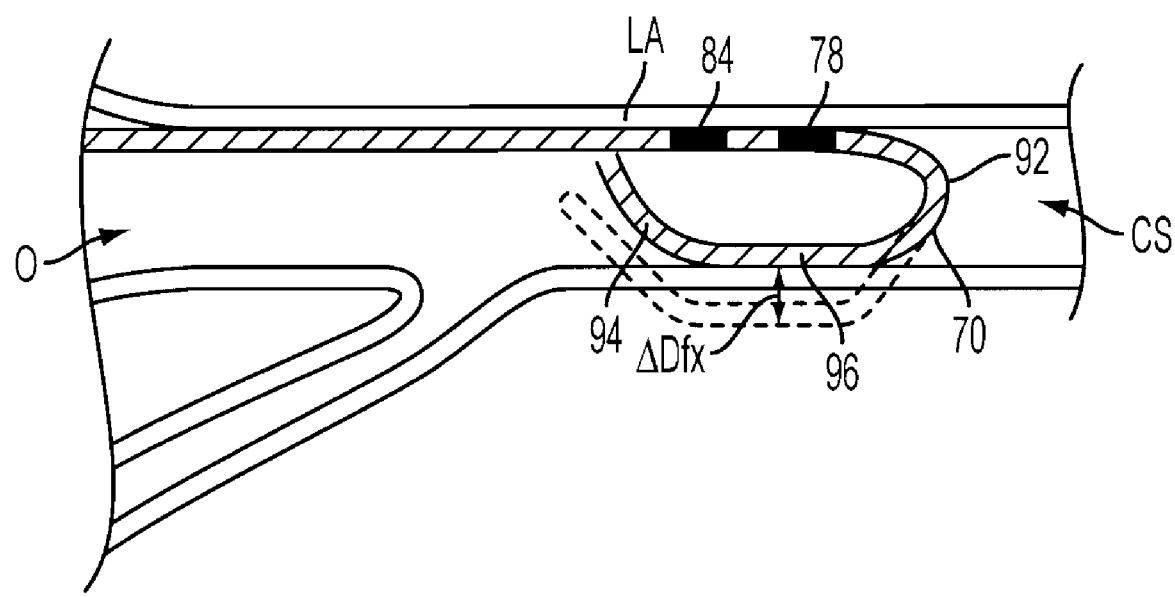
FIG. 18 is a fragmentary cross-sectional view of a coronary sinus depicting a coronary sinus pacing lead according to an embodiment of the present invention inserted into the coronary sinus.

Once the sheath 64 is held into place proximate the ostium of the coronary sinus, the stylet 60 of the pacing lead 40 is withdrawn to a position proximate the proximal portion 62 of pacing lead 40. The pacing lead 40 is then deployed out of the sheath 64. After the pacing lead 40 has been advanced out of the sheath 64 and any straightening member has been removed so that fixation element 70 takes its pre-formed loop shape with fixation element 70 in a prolapsed configuration laterally adjacent lead body 67, the lead 40 and stylet 60 are advanced into the coronary sinus, proximal portion 92 first as depicted in FIG. 17. As the pacing lead 40 is inserted into the ostium of the coronary sinus, the loop structure 96, the uncompressed width W of which is greater than the diameter D of the coronary sinus, is compressed laterally in the direction of the arrow by the walls of the coronary sinus. Once completely in place with fixation element 70 deflected inwardly by an amount $\Delta D_{fx}$ as depicted in FIG. 18, the deflection of resilient fixation element 70 biases lead body 67 and electrodes 78, 84, against the wall of the coronary sinus. The improved electrode conductive contact resulting from the biasing force applied by fixation element 70 enables lower pacing voltages and thresholds and improves lead stability. The contact also inhibits any movement of the pacing lead 40 due to the heart beating and breathing of the patient once it is in its place within the coronary sinus.

It will be readily appreciated that, in addition to the embodiments disclosed above, a pacing lead according to the invention may take a variety of alternative forms, each including a fixation element prolapsed so as to form a loop structure laterally adjacent a body portion of the lead. For the purposes of the present invention, the term loop structure includes any lead wherein the lead tip 57*a*, 102, is doubled back along the lead body and a longitudinal axis extending from the lead tip 57*a*, 102, parallels or intersects a longitudinal axis of the lead body when the tip and lead body axes are projected onto a common plane parallel to and including the lead body axis. For instance, the fixation element forming a loop structure may include a plurality of more or less straight segments angled with respect to each other, or a plurality of curved segments of various radii, a single segment with a more or less continuous curve, or a plurality of straight and curved segments joined together. The fixation element and lead body may be made with any material having suitable engineering and biocompatibility properties. The lead electrodes may take any suitable form including without limitation, coils or rings, and "buttons" or protuberances, and may be positioned on the lead body or the fixation element or any combination thereof. It may be relatively more desirable, however, to locate the electrodes proximal to any relatively sharp angles or bends in the lead so as to avoid fractures in the conductors leading to the electrodes.

While insertion of the pacing lead into the coronary sinus has been depicted and described as being done by deploying the lead outside the ostium of the coronary sinus so that lead takes its pre-formed shape before it is advanced into the coronary sinus, in other embodiments, such as where the coronary sinus has a smaller diameter, the pacing lead can be introduced tip-first in the coronary sinus in the conventional fashion.

Although the present invention has been described with reference to particular embodiments, one skilled in the art will recognize that changes may be made in form and detail without departing from the spirit and the scope of the invention. Therefore, the illustrated embodiments should be considered in all respects as illustrative and not restrictive.

What is claimed is:

1. A pacing lead for implantation in a coronary sinus having an opening and a wall defining an interior and presenting a diameter dimension, the pacing lead comprising:
    an elongated lead body defining an elongated longitudinal axis; and
    a preformed resilient fixation element extending from a distal end of the lead body and defining a loop structure laterally adjacent the lead body, wherein the loop structure terminates at a free lead tip having a lead tip axis and is configured to position the lead tip laterally adjacent to the lead body such that the lead tip axis intersects the elongated longitudinal axis of the elongated lead body wherein the lead tip points towards the elongated longitudinal axis of the elongated lead body, the pacing lead further including at least one electrode on either the lead body or the fixation element, the loop structure presenting a predetermined width dimension greater than the diameter dimension of the coronary sinus, wherein the loop structure is configured to be laterally compressed by the wall of the coronary sinus to bias the free lead tip against the wall of the coronary sinus laterally adjacent to the lead body and to bias the at least one electrode against the wall of the coronary sinus.

2. The lead of claim 1, wherein the lead includes a pair of electrodes.

3. The lead of claim 2, wherein the pair of electrodes are disposed on the lead body.

4. The lead of claim 1, wherein the loop structure includes a generally arcuate proximal portion and a generally arcuate distal portion.

5. The lead of claim 4, wherein the generally arcuate proximal portion subtends an angle of at least about 120 degrees.

6. The lead of claim 5, wherein the generally arcuate proximal portion subtends at an angle of about 180 degrees.

7. The lead of claim 4, wherein the generally arcuate distal portion subtends an angle of at least about 40 degrees.

8. The lead of claim 7 wherein the generally arcuate distal portion subtends an angle of about 90 degrees.

9. The lead of claim 4, wherein the loop structure includes a generally straight portion between the generally arcuate proximal portion and the generally arcuate distal portion.

10. The lead of claim 1, wherein the loop structure includes a generally straight proximal portion defining an angle with the pacing portion of less than 90 degrees.

11. The lead of claim 10, wherein the loop structure includes a generally straight distal portion defining an angle with the generally straight proximal portion of between about 90 and about 150 degrees.

12. The lead of claim 11, wherein the loop structure includes a generally straight portion between the generally straight proximal portion and the generally straight distal portion.

13. The lead of claim 1, wherein the lead defines a central lumen.

14. The lead of claim 13, wherein the central lumen extends through the lead body and the resilient fixation element.

15. The lead of claim 13, wherein the lead defines an aperture extending from the central lumen to an exterior surface of the lead.

16. The lead of claim 1, further comprising a catheter and a guidewire operably coupled to the catheter for guiding the lead towards the opening of the coronary sinus.

17. The lead of claim 16, wherein the lead defines an aperture extending from the central lumen to an exterior surface of the lead, the guidewire extending through the central lumen and aperture of the lead.

18. The lead of claim 1, wherein the lead comprises a lead width, the lead width being between 4 and 6 French.

19. The lead of claim 1, wherein the predetermined width dimension is between about 10% and about 200% of the diameter dimension of the coronary sinus.

20. The lead of claim 1, wherein the predetermined width dimension is between about 25% and about 75% of the diameter dimension of the coronary sinus.

* * * * *